US012685853B2

(12) United States Patent

Yang

(10) Patent No.: US 12,685,853 B2

(45) Date of Patent: Jul. 21, 2026

(54) MICRONEEDLE PATCH, MANUFACTURING MOLD THEREFOR, AND MANUFACTURING METHOD THEREFOR

(71) Applicant: Darwin Precisions Corporation, Hsinchu County (TW)

(72) Inventor: Yun-Pei Yang, Hsinchu County (TW)

(73) Assignee: DARWIN PRECISIONS CORPORATION, Hsinchu County (TW)

( * ) Notice: Subject to any disclaimer, the term of this patent is extended or adjusted under 35 U.S.C. 154(b) by 145 days.

(21) Appl. No.: 18/368,696

(22) Filed: Sep. 15, 2023

(65) Prior Publication Data

US 2024/0091515 A1 Mar. 21, 2024

(30) Foreign Application Priority Data

Sep. 16, 2022 (TW) .................................. 111135208

(51) Int. Cl.
 *A61M 37/00* (2006.01)

(52) U.S. Cl.
 CPC . *A61M 37/0015* (2013.01); *A61M 2037/0023* (2013.01); *A61M 2037/0046* (2013.01); *A61M 2037/0053* (2013.01)

(58) Field of Classification Search
 CPC ...... A61M 37/0015; A61M 2037/0053; A61M 2037/0023; A61M 2037/0046; B29L 2031/7544; A61K 9/0021
 See application file for complete search history.

(56) References Cited

U.S. PATENT DOCUMENTS 11,241,563 B2 * 2/2022 Alary ................ A61M 37/0015
11,543,433 B2 1/2023 Kim
(Continued)

FOREIGN PATENT DOCUMENTS

CN 110099714 A 8/2019
CN 112423829 A 2/2021
(Continued)

OTHER PUBLICATIONS

WO 2016010034 english language machine translation (Year: 2016).*
(Continued)

*Primary Examiner* — Wesley G Harris
(74) *Attorney, Agent, or Firm* — WPAT, PC

(57) ABSTRACT

The present invention provides a transdermally deliverable microneedle patch, a manufacturing mold therefor, and a manufacturing method therefor. The transdermally deliverable microneedle patch includes: a basal layer for attaching to an epidermis, and a microneedle array and a bump array arranged on the basal layer. The microneedle array includes a plurality of microneedles that protrude and extend away from the basal layer. The microneedles are made of a predetermined medicament and a first dissolvable carrier component, and diameters or maximum dimensions of the cross section of ends of the microneedles opposite to the basal layer are less than 50 μm. The bump array includes a plurality of bumps that protrude and extend away from the basal layer. Diameters or maximum dimensions of the cross section of ends of the bumps opposite to the basal layer are greater than 50 μm. The bumps are arranged at intervals along a periphery of the microneedle array, and heights by which the bumps protrude from the basal layer are less than heights by which the microneedles protrude from the basal layer.

7 Claims, 15 Drawing Sheets

(56)  References Cited

U.S. PATENT DOCUMENTS

| 12,036,378 B2 | 7/2024 | Lim | |
| 2008/0269685 A1 * | 10/2008 | Singh | A61K 38/29 |
| | | | 604/173 |
| 2020/0315502 A1 | 10/2020 | Samant | |

FOREIGN PATENT DOCUMENTS

| CN | 117919581 A | * | 4/2024 | A61M 37/0015 |
| JP | 2007089792 A | * | 4/2007 | A61M 37/0015 |
| KR | 20120095029 A | * | 8/2012 | A61M 37/00 |
| WO | WO-2004009172 A1 | * | 1/2004 | A61K 9/0021 |
| WO | WO-2016010034 A1 | * | 1/2016 | A61M 37/0015 |

OTHER PUBLICATIONS

JP 2007089792 english language machine translation (Year: 2007).*

JP 2007089792 A, English langauge machine translation (Year: 2007).*

China Patent Office "Office Action" issued on Jan. 26, 2025, China.

* cited by examiner

210

310

40

50

60

70

1000

S200

S200

MICRONEEDLE PATCH, MANUFACTURING MOLD THEREFOR, AND MANUFACTURING METHOD THEREFOR

CROSS-REFERENCE TO RELATED APPLICATION

This application claims the priority benefit of Taiwan application serial no. 111135208 filed on Sep. 16, 2022. The entirety of the above-mentioned patent application is hereby incorporated by reference herein and made a part of this specification.

TECHNICAL FIELD

The present invention relates to a microneedle patch, a manufacturing mold therefor, and a manufacturing method therefor. Specifically, the present invention relates to a transdermally deliverable microneedle patch with microneedles and bumps, a manufacturing mold therefor, and a manufacturing method therefor.

BACKGROUND

The microneedle patch is a newly developed transdermally deliverable medicament delivery form. Carrying on with the above, since the microneedle patch can conveniently implement subcutaneous injection with less pain through a patch, and a large number of medicines that are difficult to pierce an epidermis can be delivered into the body, the development and application of the microneedle patch have gradually attracted people's attention. However, in the application field where dosage needs to be controlled, the microneedle patch has a technical bottleneck to be overcome due to susceptibility to needle breakage. Therefore, it is expected to develop a technology that can reduce or avoid the damage of microneedles in microneedle patches, thereby improving the integrity and dosage accuracy of microneedles for medicament delivery.

SUMMARY

Technical Means for Resolving the Problems

In order to solve the above problems, a transdermally deliverable microneedle patch is provided according to an embodiment of the present invention, including: a basal layer for attaching to an epidermis; a microneedle array, arranged on the basal layer and including a plurality of microneedles that protrude and extend away from the basal layer, where the microneedles are made of a predetermined medicament and a first dissolvable carrier component, and diameters or maximum dimensions of the cross section of ends of the microneedles opposite to the basal layer are less than 50 μm; and a bump array, arranged on the basal layer and including a plurality of bumps that protrude and extend away from the basal layer, where diameters or maximum dimensions of the cross section of ends of the bumps opposite to the basal layer are greater than 50 μm. The bumps are arranged at intervals along a periphery of the microneedle array, and heights by which the bumps protrude from the basal layer are less than heights by which the microneedles protrude from the basal layer.

Another embodiment of the present invention provides a manufacturing mold for manufacturing the transdermally deliverable microneedle patch as described above, including: a mold body, provided with an accommodating cavity for application of a to-be-cured coating material, where a front side of the mold body defining the accommodating cavity is divided into a first block and a second block. The first block is provided with a plurality of first concave holes on a front side, and the second block is provided with a plurality of second concave holes on the front side. Depths of the first concave holes are greater than depths of the second concave holes. A diameter or a maximum dimension of the cross section of a deepest bottom of each of the first concave holes is less than 50 μm, and a diameter or a maximum dimension of the cross section of a deepest bottom of each of the second concave holes is greater than 50 μm. The second concave holes are arranged at intervals along a periphery of the first block.

Yet another embodiment of the present invention provides a method for manufacturing a transdermally deliverable microneedle patch by using the above manufacturing mold. The method includes: a coating step, including: filling the first concave holes with a predetermined medicament and a first dissolvable carrier component, and filling the second concave holes with the predetermined medicament and the first dissolvable carrier component, the first dissolvable carrier component, or a second dissolvable carrier component different from the first dissolvable carrier component, to complete application of the coating material of the first block and the second block; a curing step, including: curing the coating material under a predetermined condition to form a body of the transdermally deliverable microneedle patch; and a removal step, including: removing the body from the second block toward the first block to manufacture the transdermally deliverable microneedle patch. In the finally manufactured transdermally deliverable microneedle patch, the microneedles are formed corresponding to the first concave holes, and the bumps are formed corresponding to the second concave holes.

Efficacy Compared with the Prior Art

According to the transdermally deliverable microneedle patch, the manufacturing mold therefor, and the manufacturing method therefor provided in the embodiments of the present invention, the unexpected damage, bending, indentation, or fracture of the delivery microneedles can be reduced or avoided, and therefore, a dosage of a medicament expected to be administered to a user can be more accurately controlled by a plurality of microneedles. Carrying on with the above, the transdermally deliverable microneedle patch, the manufacturing mold therefor, and the manufacturing method therefor according to the embodiments of the present invention can be applied to the fields of medicine, aesthetic medicine, vaccines, and the like that require more accurate dosage control, so as to realize more convenient and accurate transdermal medicine delivery.

DETAILED DESCRIPTION

Various embodiments are to be described below, and a person with ordinary knowledge in the art can easily understand the spirit and principles of the present invention by referring to the accompanying drawings. However, although some specific embodiments are to be specifically described herein, these embodiments are only illustrative and are not to be considered restrictive or exhaustive in all aspects. Therefore, various changes and modifications of the present invention should be obvious and easily achieved for those with ordinary knowledge in the art without departing from the spirit and principles of the present invention.

Figure 1:
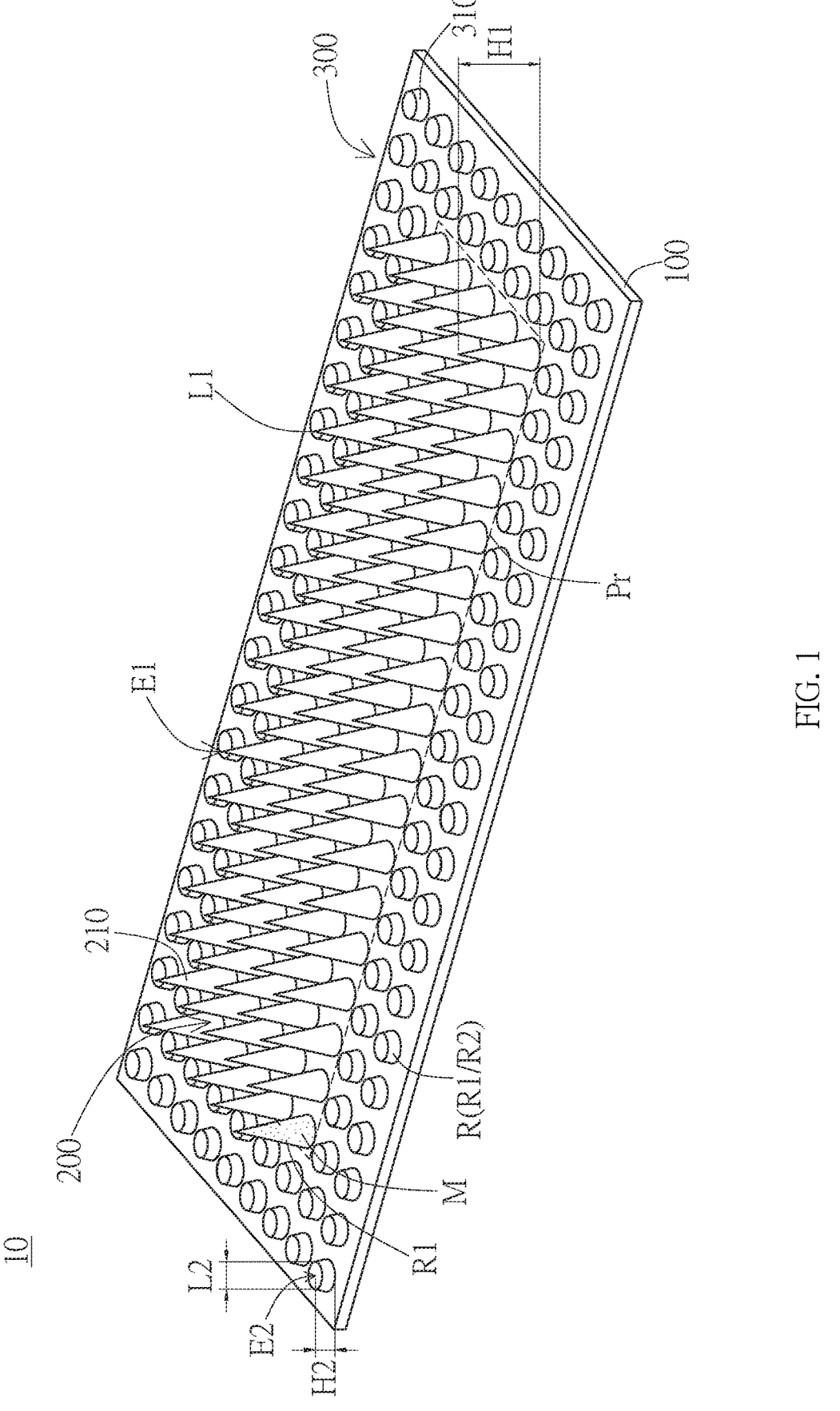
FIG. 1 is a three-dimensional schematic diagram of a transdermally deliverable microneedle patch according to an embodiment of the present invention.
Figure 2:
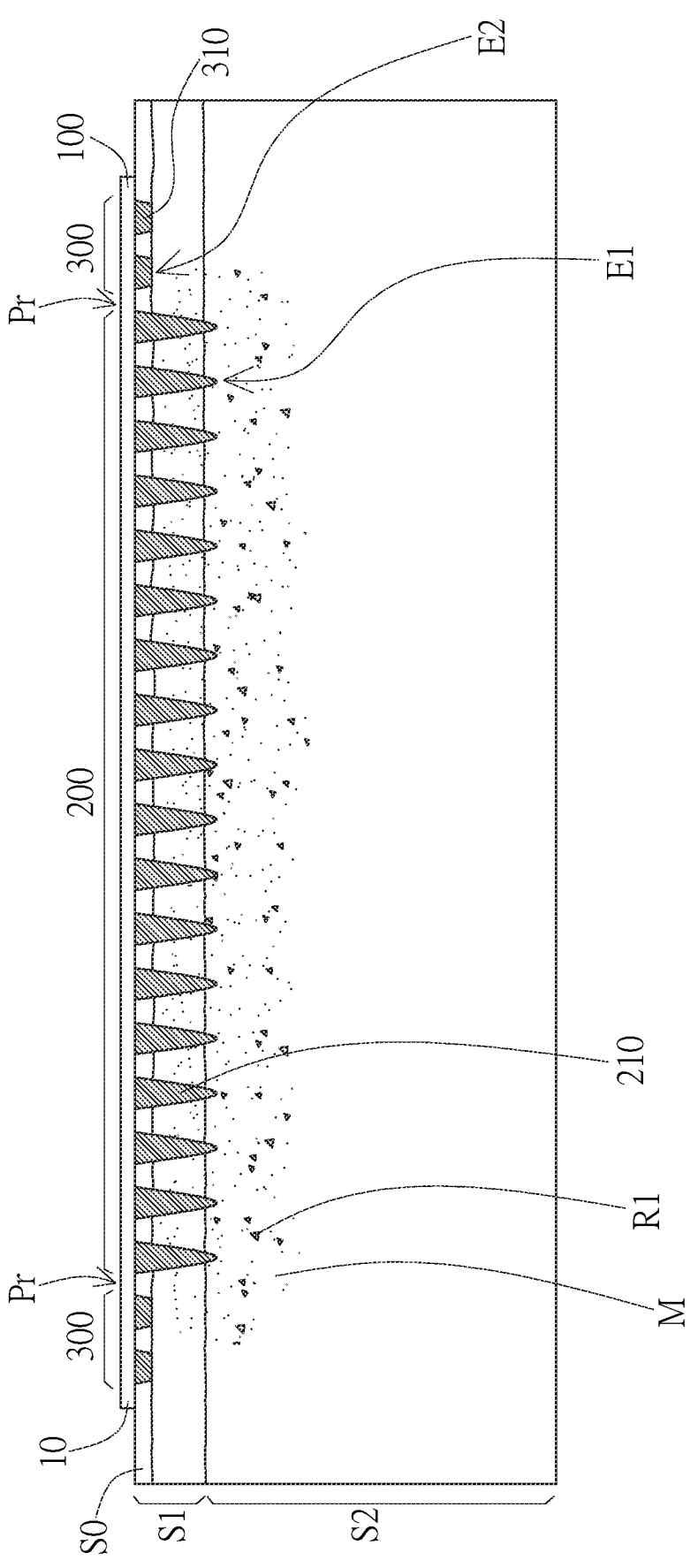
FIG. 2 is a schematic diagram of application of a transdermally deliverable microneedle patch according to an embodiment of the present invention.
Figure 3:
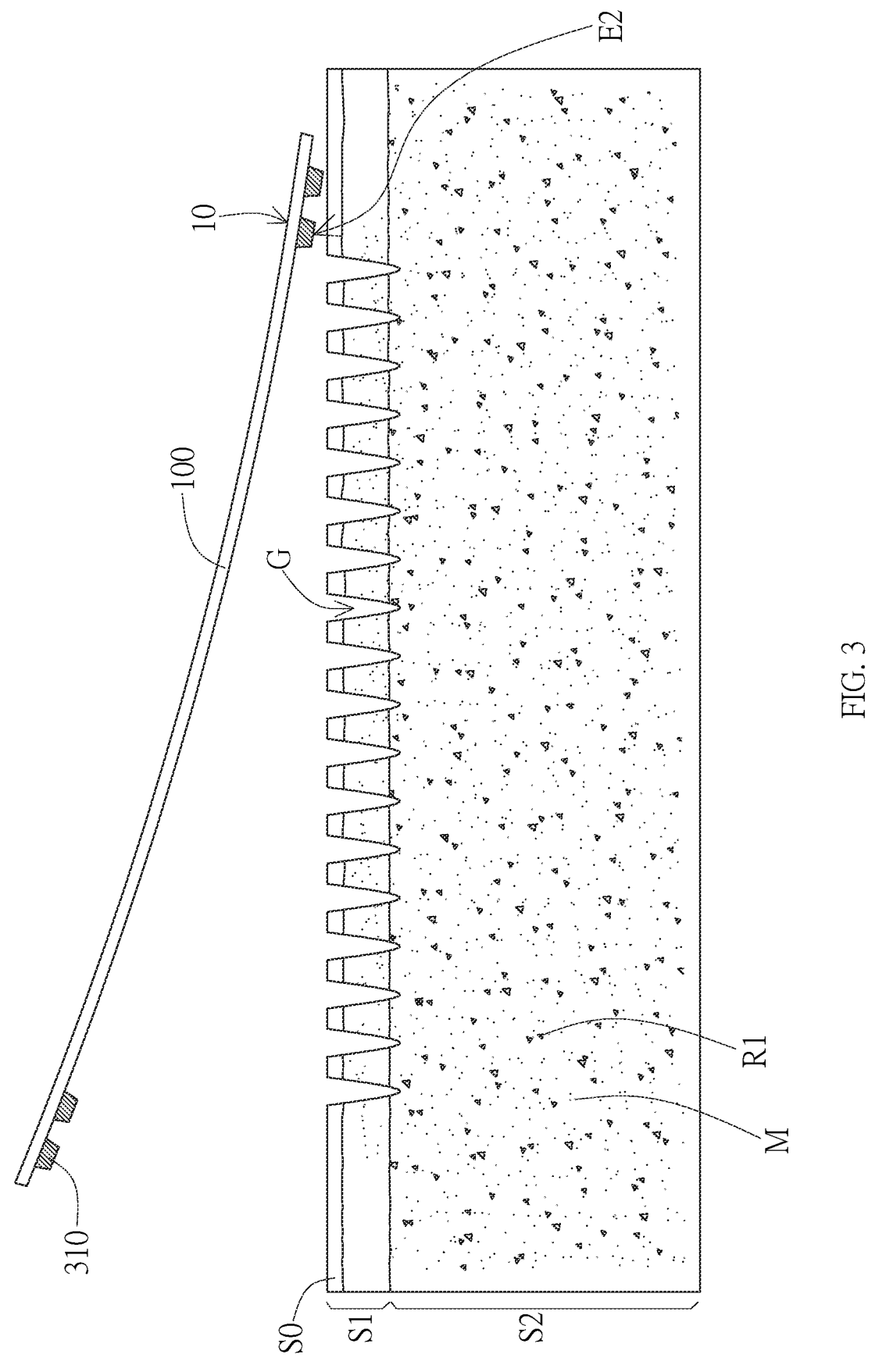
FIG. 3 is a schematic diagram of application completion of a transdermally deliverable microneedle patch according to an embodiment of the present invention.

Referring to FIG. 1, according to an embodiment of the present invention, a transdermally deliverable microneedle patch 10 is provided, which can reduce or avoid the damage, bending, indentation, or fracture of microneedles 210 therein. The transdermally deliverable microneedle patch 10 may include a basal layer 100 for attaching to an epidermis, a microneedle array 200 arranged on the basal layer 100, and a bump array 300 arranged on the basal layer 100. In detail, referring to FIG. 2 and FIG. 3 together with FIG. 1, according to the transdermally deliverable microneedle patch 10 of this embodiment, the microneedle array 200 may include a plurality of microneedles 210 configured to deliver a predetermined medicament M. As shown in FIG. 2, the plurality of microneedles 210 may be configured to pierce an epidermis S1 (including stratum corneum S0) and reach a dermis S2 to release the predetermined medicament M. For example, according to this embodiment, the transdermally deliverable microneedle patch 10 may include soluble microneedles, and the microneedles 210 are made of a predetermined medicament M and a first dissolvable carrier component R1. After piercing the epidermis S1, as shown in FIG. 2 and FIG. 3, the first dissolvable carrier component R1 is dissolvable and releases the predetermined medicament M coated therein into the body based on a body temperature and body fluids. In this way, administration of the predetermined medicament M can be completed through transdermal delivery.

Carrying on with the above, the plurality of microneedles 210 may protrude and extend away from the basal layer 100, and diameters or maximum dimensions L1 of the cross section of ends E1 of the microneedles 210 opposite to the basal layer 100 may be less than 50 um. Therefore, the plurality of microneedles 210 may be made sharp enough to easily pierce the barrier of the epidermis S1 and enter the dermis S2. Based on the above, the microneedles 210 may be configured with a predetermined dosage in advance, so that a predetermined dosage of predetermined medicament M can be administered to a user after the transdermally deliverable microneedle patch 10 is attached to the user.

In addition, according to some embodiments, in order to maintain sufficient hardness and stability, the diameters or maximum dimensions L1 of the cross section of the ends E1 of the microneedle 210 opposite to the basal layer 100 may be at least greater than 3 μm.

Further, according to this embodiment, in order to avoid the possible stress that may damage the plurality of microneedles 210 and change the predetermined dosage when the basal layer 100 is dented, bent, or torn, the bump array 300 may include a plurality of bumps 310 arranged at intervals along a periphery Pr of the microneedle array 200. As described above, like the microneedles 210, the bumps 310 may also extend and protrude away from the basal layer 100. However, diameters or maximum dimensions L2 of the cross section of ends E2 of the bumps 310 opposite to the basal layer 100 may be greater than 50 μm, and heights H2 by which the bumps 310 protrude from the basal layer 100 may be less than heights H1 by which the microneedles 210 protrude from the basal layer 100. Therefore, referring to FIG. 2 and FIG. 3, when the microneedles 210 pierce the epidermis S1 and reach the dermis S2, the bumps 310 are difficult to pierce the relatively hard stratum corneum S0, and even if the bumps pierce the stratum corneum S0, the heights H2 of the bumps cannot reach the depth of the dermis S2, so that the bumps 310 may not pierce the epidermis SI including the stratum corneum SO and reach the dermis S2.

For example, according to some embodiments, the heights H1 by which the microneedles 210 protrude from the basal layer 100 may be between 100 μm and 1500 μm. For example, the heights H1 by which the microneedles 210 protrude from the basal layer 100 may be between 150 μm and 1000 μm. In contrast, the heights H2 by which the bumps 310 protrude from the basal layer 100 may be between 10 μm and 150 μm. For example, the heights H2 by which the bumps 310 protrude from the basal layer 100 may be between 30 μm and 50 μm. As described above, with this configuration, the bumps 310 will not have the ability to pierce and reach the dermis S2.

Carrying on with above, since a plurality of bumps 310 are arranged around the microneedles 210, the stress transmitted along the basal layer 100, such as the stress that may be transmitted along the basal layer 100 during operations such as applying pressure to, removing, attaching the basal layer 100, may be reduced or prevented from being directly transmitted to the microneedles 210. For example, these stresses or impacts may be transmitted to the bumps 310 first, and may be reduced or prevented from being further transmitted to the microneedles 210 through buffering or absorption of the bumps 310. Alternatively, the stress may be prevented from being directly applied to a turning point where the microneedles 210 are connected to the basal layer 100 along a linear contour of the basal layer 100. Through the changes in the contour of the bumps 310 with lower heights H2, the direction of the stress transmission can be guided and altered and then transmitted to the microneedles 210. Therefore, the unexpected damage, bending, indentation, or fracture caused by direct impact or application of unexpected stress on the microneedles 210 may be reduced or avoided. Therefore, before the microneedles 210 enter the dermis S2 to deliver the predetermined medicament M, the unnecessary loss of the predetermined medicament M or the loss of the piercing function of the microneedles 210 can be reduced or avoided, so that the administration of the predetermined dosage of predetermined medicament M can be realized through the transdermally deliverable microneedle patch 10 of this embodiment.

According to some embodiments, the bump 310 may be damaged, bent, dented, or broken due to being subjected to stress. However, the damage, bending, indentation, or fracture of the bump 310 will not affect or change the dosage of the predetermined medicament M that is finally expected to be administered.

Carrying on with above, the microneedle array 200 may be arranged in an effective area of the transdermally deliverable microneedle patch 10 expected to play the role of administration, and the above bump array 300 may be arranged in another area of the transdermally deliverable microneedle patch 10 not expected to play the role of administration. However, the above are merely examples, and the present invention is not limited thereto. A person of ordinary skill in the art may arrange any area of the microneedle array 200 in the transdermally deliverable microneedle patch 10 as required, so that the periphery Pr of the microneedle array 200 corresponding to the effective area is at least partially provided with the bump array 300 to protect the microneedle array 200, thereby ensuring the dosage accuracy of the predetermined medicament M of the microneedle array 200.

According to some embodiments, the bumps 310 may also be made of a predetermined medicament M and a first dissolvable carrier component R1. However, the predetermined medicament M and the first dissolvable carrier component R1 contained in the bumps 310 are not to be released into the body without piercing the epidermis S1 and reaching the dermis S2. For example, without piercing the epidermis S1 (for example, only pressing and deforming the epidermis S1 without piercing the epidermis S1), the bumps 310 will not release the predetermined medicament M due to dissolution as a result of the body fluid and the body temperature.

In addition, according to some other embodiments, the bumps 310 may be made of any carrier component R without containing the predetermined medicament M. The carrier component R may be another non-dissolvable or dissolvable carrier component. For example, the carrier component R may be a first dissolvable carrier component R1 or a second dissolvable carrier component R2 different from the first dissolvable carrier component R1.

As shown in FIG. 3, in a case that the transdermally deliverable microneedle patch 10 of this embodiment is a dissolvable microneedle patch, after the microneedles 210 pierce and dissolve to release the predetermined medicament M, the basal layer 100 and the bumps 310 thereon (predetermined to abut against or press and deform the epidermis S1 without piercing the epidermis S1) may be removed to complete the administration of the predetermined dosage of the predetermined medicament M. Carrying on with the above, in this case, although through holes G through which the microneedles 210 pass may be left on the epidermis S1, these through holes G do not touch nerves, and therefore do not cause pain, and can heal quickly based on the body mechanism.

Figure 4A:
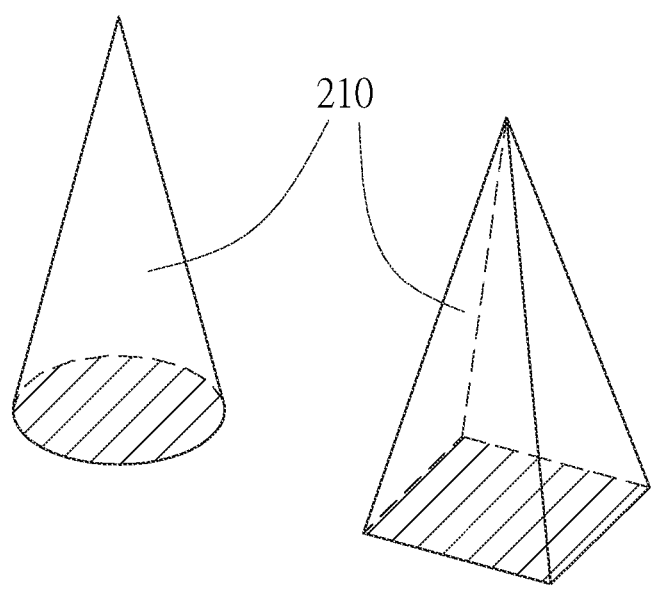
FIG. 4A is a schematic diagram of shapes and implementations of microneedles of a transdermally deliverable microneedle patch according to various embodiments of the present invention.
Figure 4B:
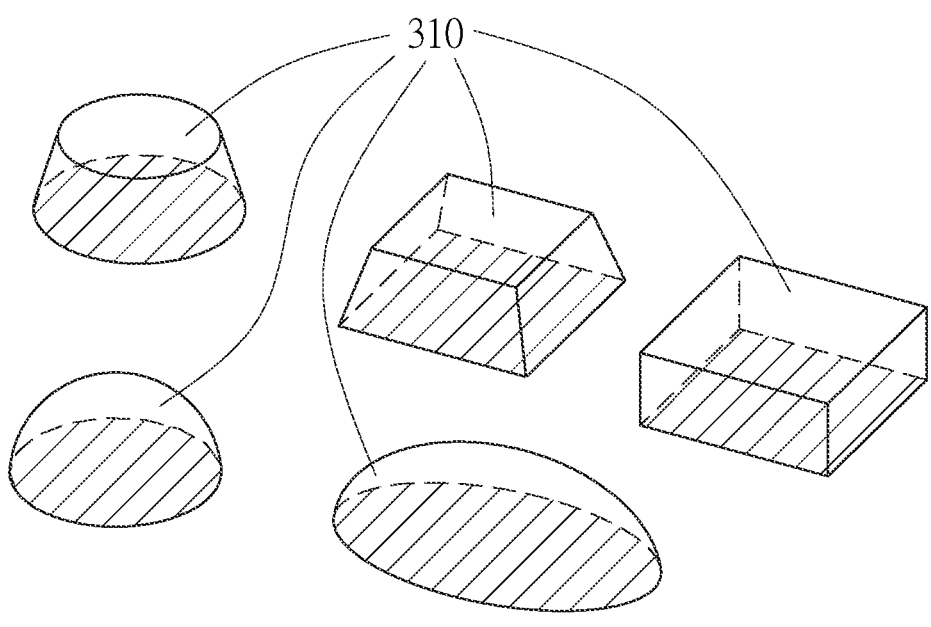
FIG. 4B is a schematic diagram of shapes and implementations of bumps of a transdermally deliverable microneedle patch according to various embodiments of the present invention.
Figure 5:
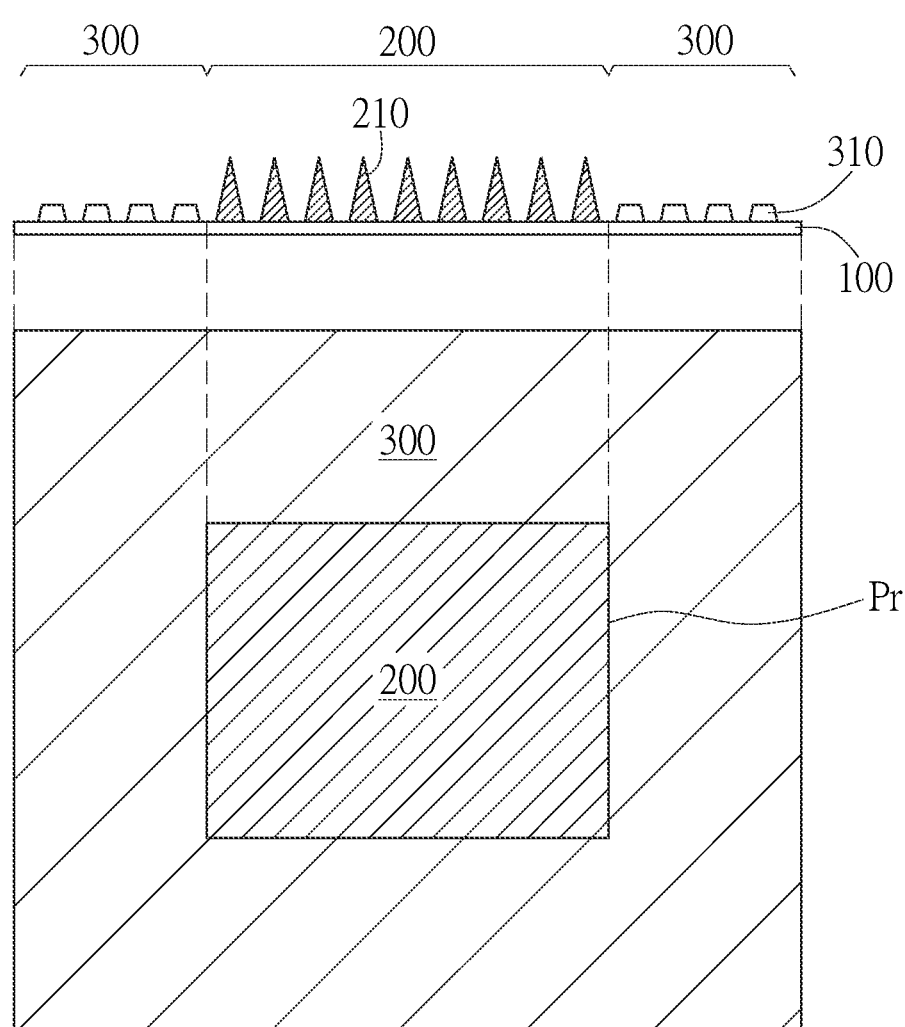
FIG. 5 is a diagram showing a relative arrangement of a microneedle array and a bump array of a transdermally deliverable microneedle patch according to an embodiment of the present invention.

Next, referring to FIG. 4A, according to some embodiments, the microneedles 210 may be polygonal pyramids or cones. However, the present invention is not limited thereto, and the microneedles 210 according to other embodiments may be any structural body that can easily pierce the epidermis S1 and reach the dermis S2. In addition, referring to FIG. 4B, according to some embodiments, the bumps 310 are polygonal columns, cylinders, incomplete spheres, or incomplete ellipsoids. However, the present invention is not limited thereto, and the bumps 310 according to another embodiment may be any structural body arranged in advance in such a way that the structural body does not pierce into the epidermis S1 including the stratum corneum S0 and reach the dermis S2.

Next, various implementations of the relative arrangement of the microneedle array 200 and the bump array 300 according to other embodiments of the present invention are described with reference to FIG. 5 to FIG. 8C.

As described above, according to various embodiments of the present invention, the bumps 310 may be arranged at intervals along a periphery Pr of the microneedle array 200. That is to say, the bump array 300 may be arranged on the periphery Pr of the microneedle array 200. Therefore, the stress transmitted from the outside through the basal layer 100 may reach the bump array 300 before reaching the microneedle array 200 to be properly guided or partially absorbed or relieved. For example, referring to FIG. 5, a transdermally deliverable microneedle patch 20 according to an embodiment may be rectangular, the microneedle array 200 may be arranged as a central rectangular block, and the bump array 300 may be a rectangular annular block surrounding the central rectangular block of the microneedle array 200.

Figure 6:
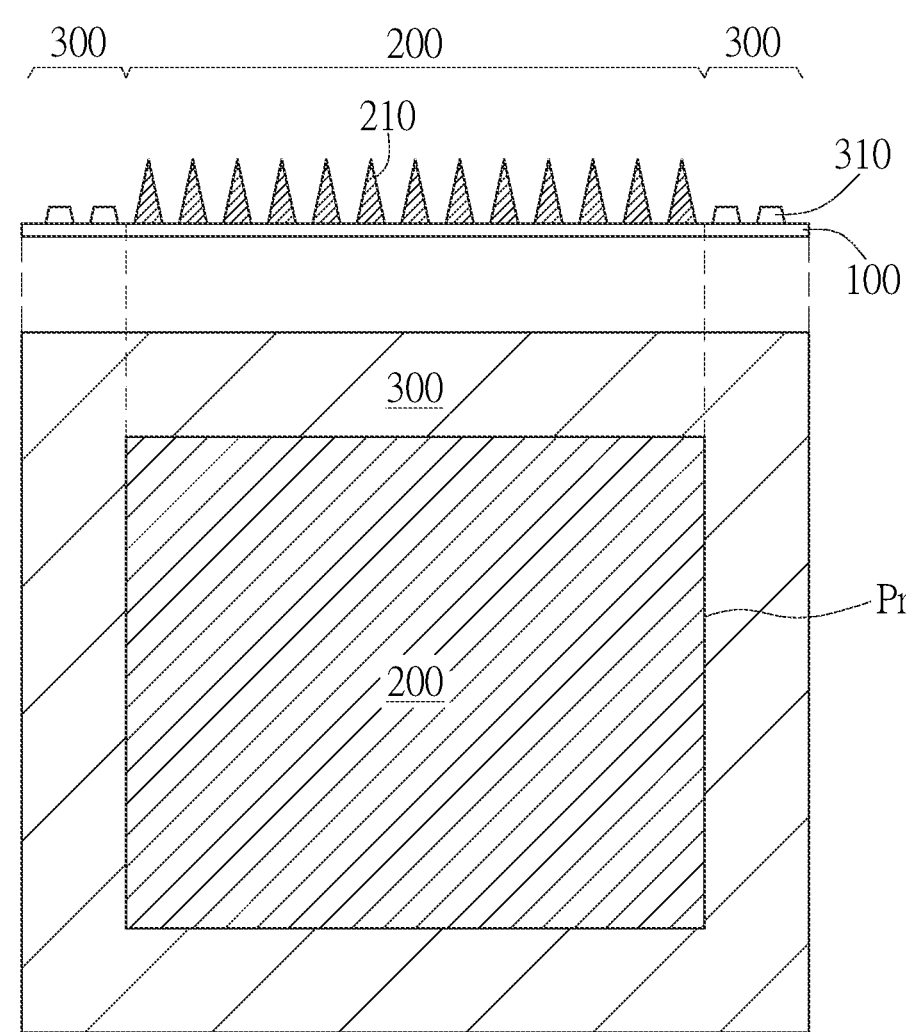
FIG. 6 is a diagram showing a relative arrangement of a microneedle array and a bump array of a transdermally deliverable microneedle patch according to another embodiment of the present invention.

Next, as shown in FIG. 6, a difference between a transdermally deliverable microneedle patch 30 according to another embodiment and the above transdermally deliverable microneedle patch 20 lies in a size of a relative occupied area between the bump array 300 and the microneedle array 200. For example, the area occupied by the microneedle array 200 can be increased, and the area occupied by the bump array 300 can be reduced. Carrying on with the above, in a case that the bump array 300 is distributed on the periphery Pr of the microneedle array 200, the relative occupied area between the bump array 300 and the microneedle array 200 may be adjusted without exceeding the scope of the present invention.

Figure 7:
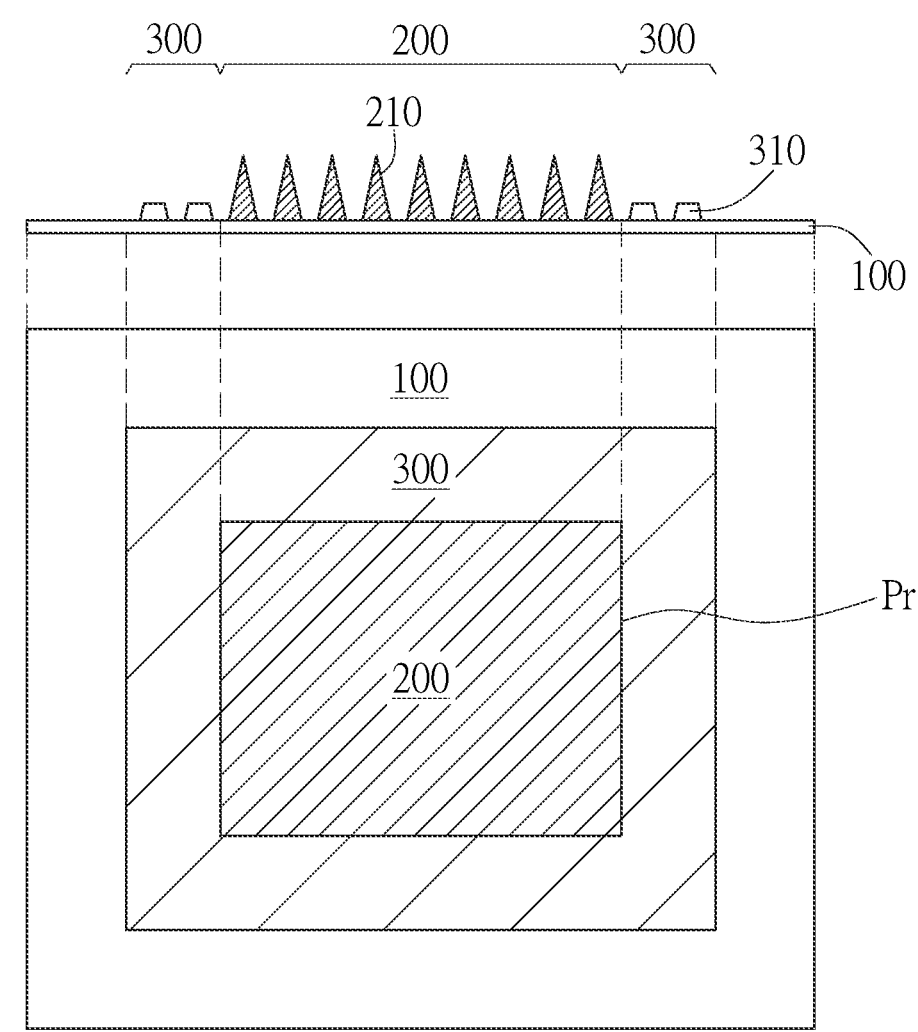
FIG. 7 is a diagram showing a relative arrangement of a microneedle array and a bump array of a transdermally deliverable microneedle patch according to still another embodiment of the present invention.

Moreover, as shown in FIG. 7, a difference between a transdermally deliverable microneedle patch 40 according to yet another embodiment and the above transdermally deliverable microneedle patch 20 is that the bump array 300 surrounding the periphery Pr of the microneedle array 200 may not be completely arranged on the basal layer 100 other than the microneedle array 200. As described above, the bump array 300 may be arranged in a partial or complete area on the basal layer 100 when being arranged on the periphery Pr of the microneedle array 200.

Figure 8A:
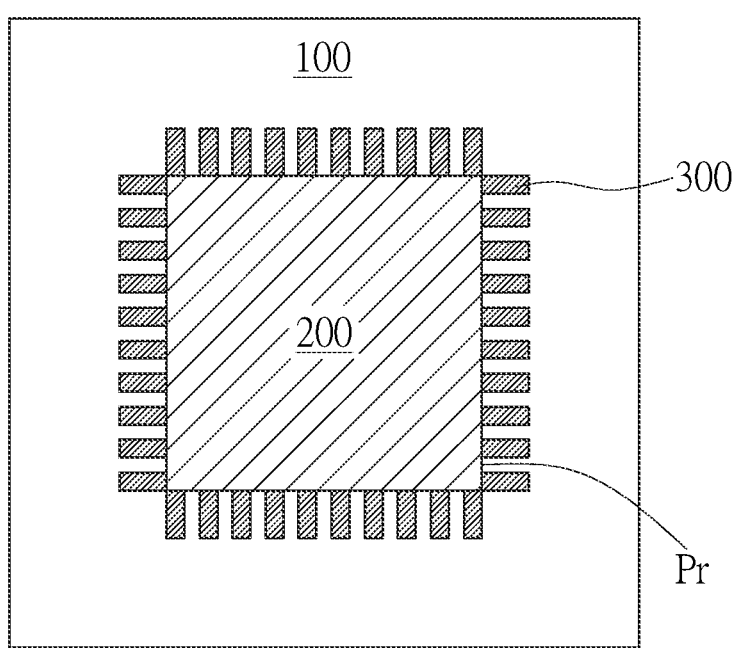
FIG. 8A to FIG. 8C are diagrams showing relative arrangements of a microneedle array and a bump array of a transdermally deliverable microneedle patch according to other embodiments of the present invention.

Next, as shown in FIG. 8A, a difference between a transdermally deliverable microneedle patch 50 according to another embodiment and the above transdermally deliverable microneedle patch 40 is that the distribution of the bumps 310 of the bump array 300 arranged along the periphery Pr of the microneedle array 200 may vary in density. For example, as shown in FIG. 8A, a bump array 300 composed of the bumps 310 may be distributed on a local periphery Pr of the microneedle array 200, and a part of the local periphery Pr of the microneedle array 200 is not provided with the bump array 300 composed of the bumps 310. For example, the bump arrays 300 may be arranged at intervals in a rectangular ring pattern along the periphery Pr of the microneedle array 200. Therefore, the cost of arranging the bumps 310 can be reduced, and the purpose of roughly arranging the bump array 300 around the microneedle array 200 to protect the microneedle array 200 can be achieved.

Further, according to some embodiments, the bump array 300 may also be formed by locally arranging bumps 310 on the periphery Pr of the microneedle array 200 according to a direction or range in which stress is most likely to occur in the operation setting. Therefore, the cost of arranging the bumps 310 may be reduced, and the bumps 310 may be arranged based on the expected operation design of the transdermally deliverable microneedle patch, thereby achieving the purpose of protecting the microneedle array 200 through the bump array 300.

Figure 8B:
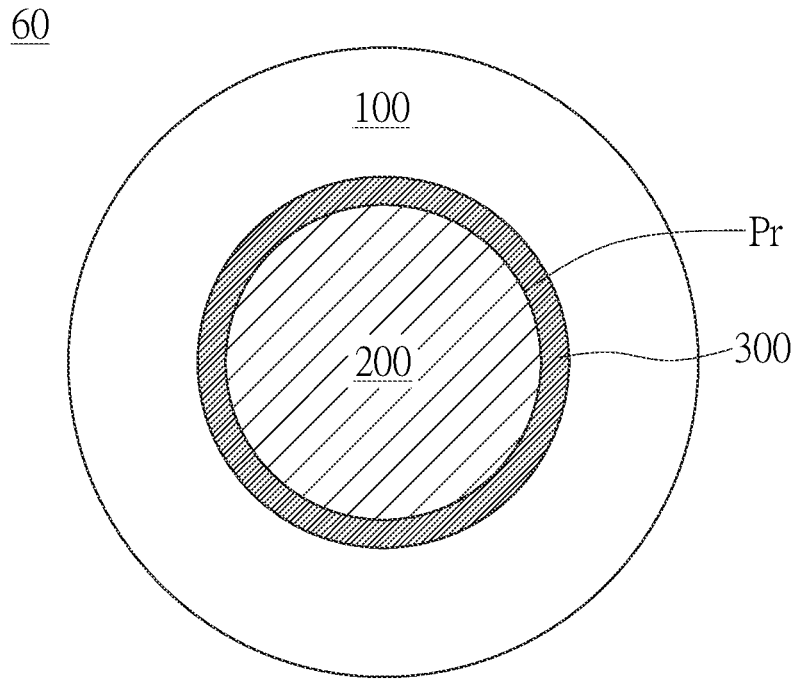
Figure 8C:
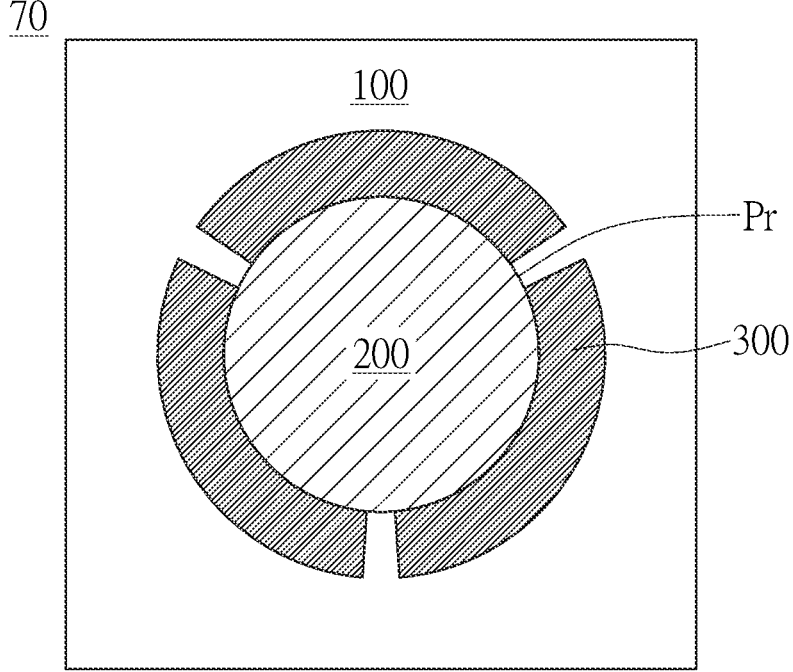

In addition, the arrangement and shapes of the bump array 300, the microneedle array 200, and the whole transdermally deliverable microneedle patch may be adjusted according to factors such as the expected removal method, the material of the microneedles 210, or the material of the basal layer 310 depending on requirements. For example, as shown in FIG. 8B, the transdermally deliverable microneedle patch 60 may be arranged such that the whole transdermally deliverable microneedle patch 60 and the microneedle array 200 are circular, and the bump array 300 is arranged around the periphery Pr of the microneedle array 200 in a ring shape. Alternatively, as shown in FIG. 8C, the transdermally deliverable microneedle patch 70 may be arranged such that the whole transdermally deliverable microneedle patch 70 is rectangular and the microneedle array 200 is circular, and the bump array 300 is partially arranged around the periphery Pr of the microneedle array 200 in a notched ring shape.

Next, a method for manufacturing a transdermally deliverable microneedle patch according to an embodiment of the present invention is to be described.

Figure 9:
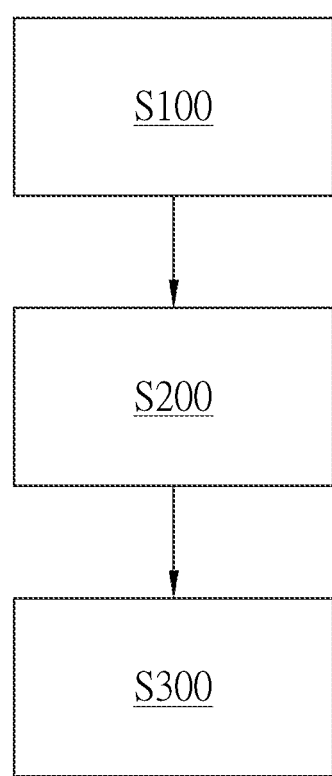
FIG. 9 is a schematic flowchart of a method for manufacturing a transdermally deliverable microneedle patch according to an embodiment of the present invention.
Figure 10:
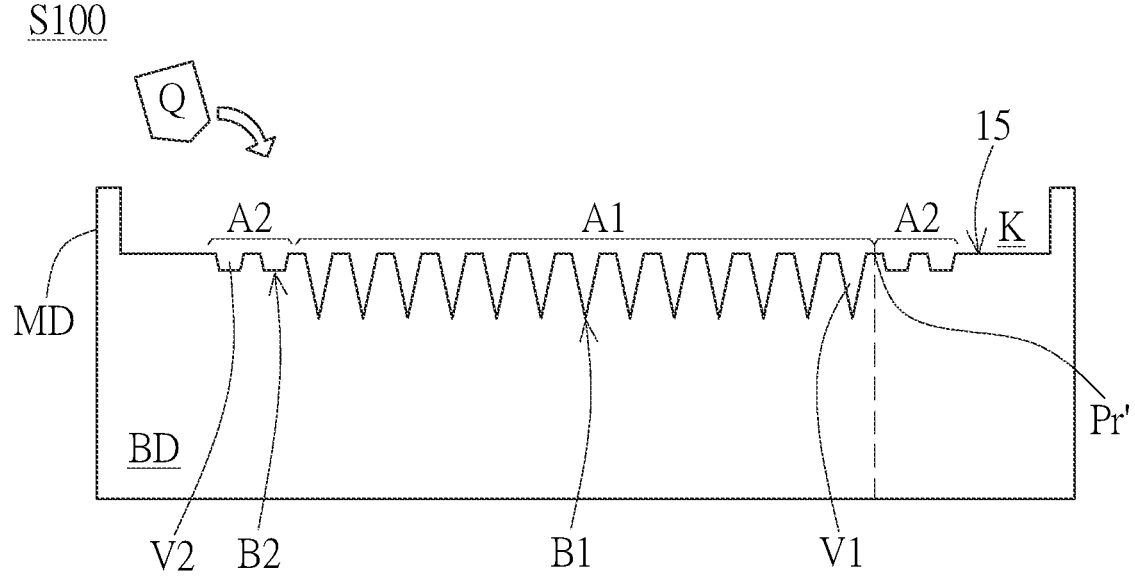
FIG. 10 is a schematic diagram of using a manufacturing mold to implement a method for manufacturing a transdermally deliverable microneedle patch according to an embodiment of the present invention.

Carrying on with the above, according to an embodiment, referring to FIG. 9, the method 1000 for manufacturing a transdermally deliverable microneedle patch may include at least a coating step S100, a curing step S200, and a removal step S300. In detail, according to an embodiment, a manufacturing mold MD may be used to manufacture the transdermally deliverable microneedle patch of the embodiments of the present invention. Carrying on with the above, as shown in FIG. 10, the manufacturing mold MD may include a mold body BD. The mold body BD may be provided with an accommodating cavity K for application of a to-be-cured coating material Q (in coating step S100). Specifically, the mold body BD may have a front side 15 for defining the accommodating cavity K and a back side 25 facing away from the front side 15. The front side 15 defining the accommodating cavity K may be further divided into at least a first block A1 and a second block A2. The first block A1 is provided with a plurality of first concave holes V1 on the front side 15, and the second block A2 is provided with a plurality of second concave holes V2 on the front side 15. According to this embodiment, these second concave holes V2 may be arranged at intervals along a periphery Pr' of the first block A1.

Carrying on with the above, the manufacturing mold MD may be made of any material that can be fixedly molded and filled with the coating material Q without being affected, for example, but not limited to metal or PDMS. In addition, the manufacturing mold MD itself may be a male mold or a female mold generated from the male mold through mold reproduction, such as electroforming or potting. Carrying on with the above, on the premise that the manufacturing mold MD with the above characteristics can be manufactured, the manner and mode of manufacturing the manufacturing mold MD according to the embodiments of the present invention may not be limited to the specifically stated implementation herein.

Figure 11:
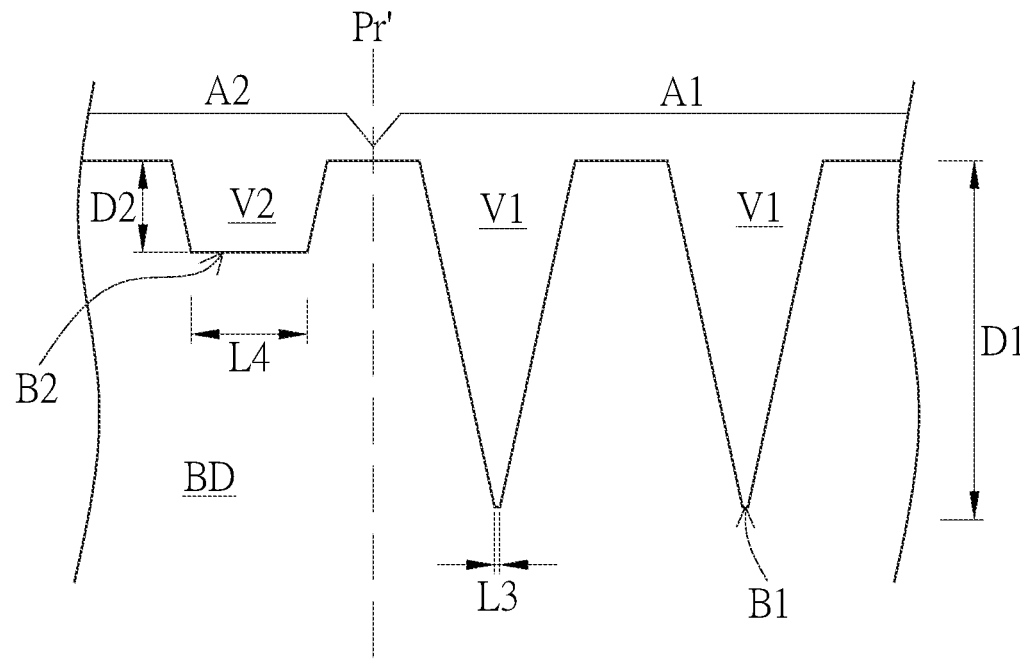
FIG. 11 is a partially schematic enlarged view of the manufacturing mold shown in FIG. 10 according to an embodiment of the present invention.

Carrying on with the above, referring to the partial enlarged view of FIG. 11 together with FIG. 10, according to this embodiment, depths DI of the first concave holes V1 are greater than depths D2 of the second concave holes V2. Moreover, a diameter or a maximum dimension L3 of the cross section of a deepest bottom B1 of each of the first concave holes V1 may be less than 50 μm, and a diameter or a maximum dimension L4 of the cross section of a deepest bottom B2 of each of the second concave holes V2 may be greater than 50 μm. In addition, according to some embodiments, a diameter or a maximum dimension L3 of the cross section of a deepest bottom BI of each of the first concave holes V1 may be greater than 3 μm.

Carrying on with the above, according to some embodiments, the depths D1 of the first concave holes V1 may be between 100 nm and 1500 μm. For example, the depths D1 of the first concave holes V1 may be between 150 nm and 1000 μm. In contrast, the depths D2 of the second concave holes V2 may be between 10 nm and 150 μm. For example, the depths D2 of the second concave holes V2 may be between 30 μm and 50 μm. In addition, although not specifically illustrated herein, according to other embodiments, the first concave holes V1 may be polygonal cones or cones, and the second concave holes V2 may be polygonal cylinders, cylinders, incomplete spheroids, or incomplete ellipsoids. Carrying on with the above, with reference to the above description, a person of ordinary skill in the art may understand that with this configuration, the microneedles 210 formed corresponding to the first concave holes V1 and the bumps 310 formed corresponding to the second concave holes V2 may be manufactured.

Figure 12:
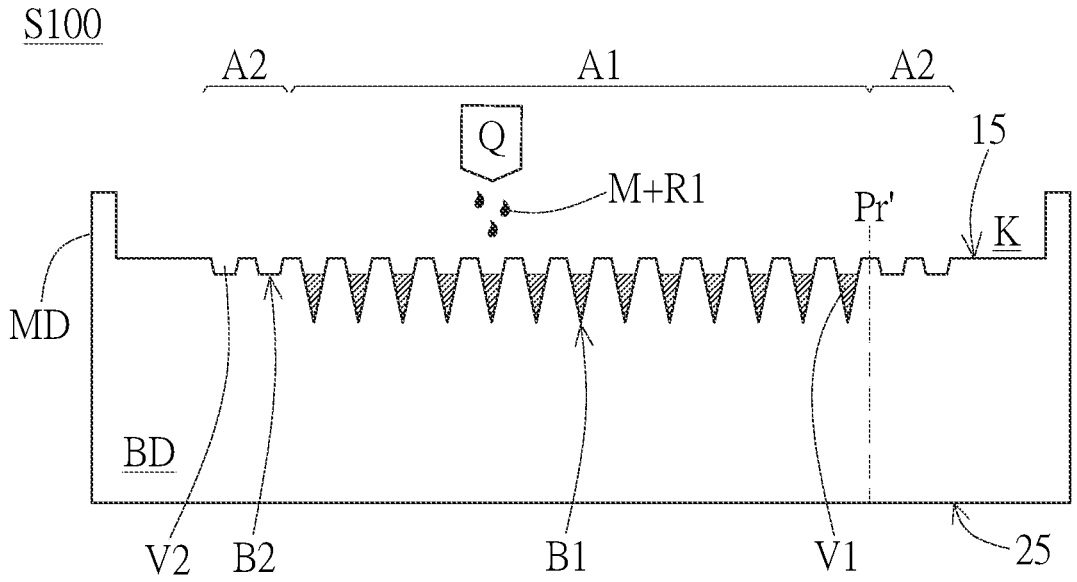
FIG. 12 is a schematic diagram of implementing a coating step of a manufacturing method according to an embodiment of the present invention.
Figure 13:
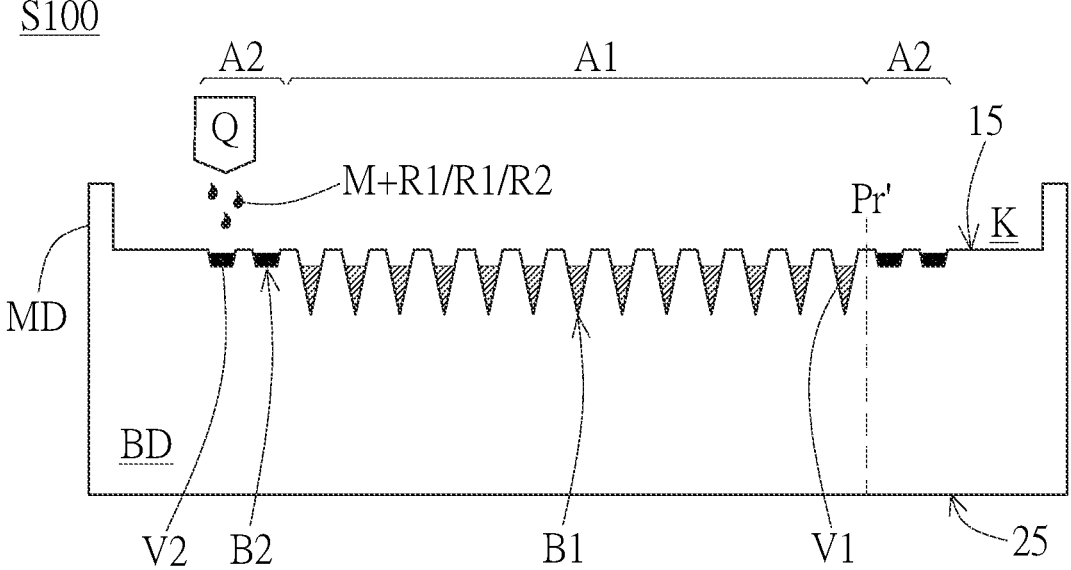
FIG. 13 is a schematic diagram of implementing a coating step of a manufacturing method according to an embodiment of the present invention.

Next, referring to FIG. 12, according to an embodiment, the manufacturing mold MD may be used to manufacture the transdermally deliverable microneedle patch. Specifically, as shown in FIG. 12, in the coating step S100, the first concave holes V1 may be filled with a predetermined medicament M and a first dissolvable carrier component R1. Next, as shown in FIG. 13, in the coating step S100, the second concave holes V2 may be filled with a predetermined medicament M and a first dissolvable carrier component R1, a first dissolvable carrier component R1, or a second dissolvable carrier component R2 different from the first dissolvable carrier component R1. In addition, in the coating step S100, after the first concave holes V1 and the second concave holes V2 are at least partially filled, the accommodating cavity may be coated across the first block A1 and the second block A2 with a predetermined medicament M and a first dissolvable carrier component R1, a first dissolvable carrier component R1, a second dissolvable carrier component R2, or a third dissolvable carrier component R3 different from the first dissolvable carrier component R1 and the second dissolvable carrier component R2. Alternatively, any carrier component may be adopted to coat the accommodating cavity K across the first block A1 and the second block A2. Carrying on with the above, coated parts other than the first concave holes V1 and the second concave holes V2 may also be cured and formed in the subsequent curing step S200, so as to form the basal layer 100 of the transdermally deliverable microneedle patch.

Figure 14A:
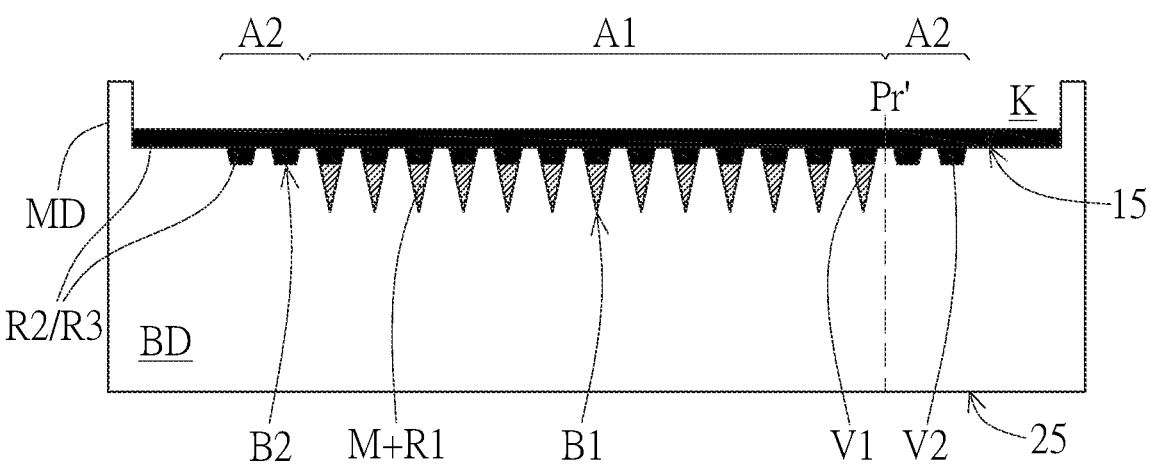
FIG. 14A and FIG. 14B are schematic diagrams of a curing step upon completion of the coating step according to different embodiments of the present invention.

For example, according to an embodiment, as shown in FIG. 14A, the first concave holes V1 may be filled with the predetermined medicament M and the first dissolvable carrier component R1, and then the second concave holes V2 and some spaces of the accommodating cavity K other than the first concave holes V1 and the second concave holes V2 may be filled with the second dissolvable carrier component R2 or the third dissolvable carrier component R3. Carrying on with the above, the application of the coating material Q of the first block A1 and the second block A2 may be completed accordingly, and then the curing step S200 is performed. In this way, the most suitable material may be configured corresponding to the characteristics of each part of the to-be-formed finished product. However, the above are merely examples, and other embodiments of the present invention are not limited thereto. For example, referring to FIG. 14B again, the first concave holes V1, the second concave holes V2, and some spaces of the accommodating cavity K other than the first concave holes V1 and the second concave holes V2 may also be directly filled with the predetermined medicament M and the first dissolvable carrier component R1. Carrying on with the above, the application of the coating material Q of the first block A1 and the second block A2 may be completed accordingly, and then the curing step S200 is performed. In this way, application of all parts may be directly completed by using the same material, so as to reduce or avoid the procedures and efforts required for preparing materials and changing materials. However, this is only an example, and the process, sequence, and materials for filling the first concave holes V1 and the second concave holes V2 and other spaces of the accommodating cavity K in other embodiments of the present invention are not limited to the specifically stated implementation in line with scientific principles and the scope of the present invention.

Carrying on with the above, in the curing step S200, curing may be performed under a predetermined condition based on the curing characteristics of the coated or filled materials. For example, the materials filled in the first concave holes V1, the second concave holes V2, and other spaces of the accommodating cavity K may be air-dried and cured under the predetermined air-drying condition.

In addition, the carrier component mentioned in the above embodiments may be any pharmaceutical-grade carrier component that is harmless to the body and can swell or dissolve in the skin. Carrying on with the above, in the case of coating or carrying the predetermined medicament M, the coated or carried predetermined medicament M may be released through the swelling or dissolution of the carrier component, and diffused into the body to achieve the predetermined effect of administration.

Carrying on with the above, according to some embodiments, various carrier components such as, but not limited to, maltose, sucrose, maltodextrin, hyaluronic acid, methylcellulose, chitosan, gelatin, polylactic acid, or hydroxypropyl methylcellulose may be used to manufacture the transdermally deliverable microneedle patch. However, the embodiments of the present invention are not limited thereto, and various carrier components that can be used to manufacture the transdermally deliverable microneedle patch may have various changes during the implementation of the present invention.

Figure 14B:
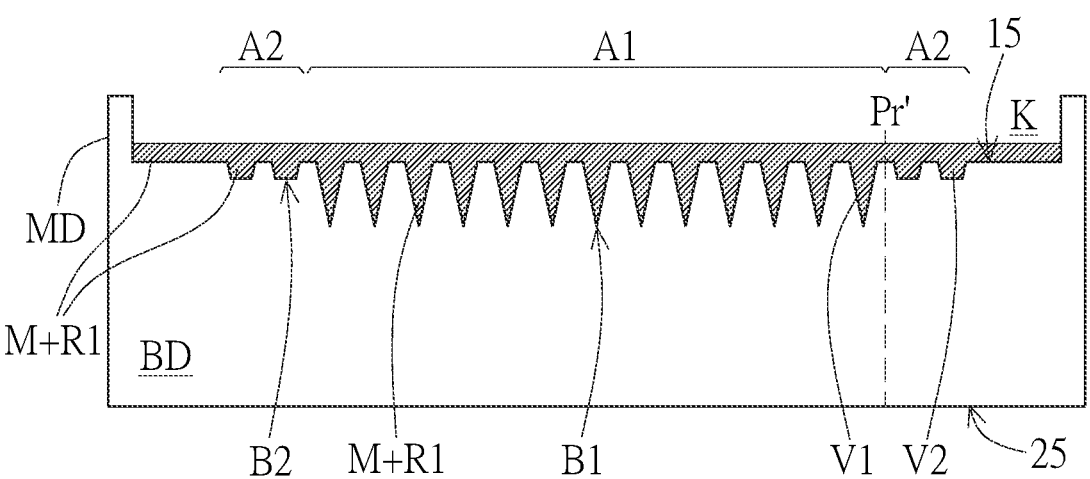
Figure 15:
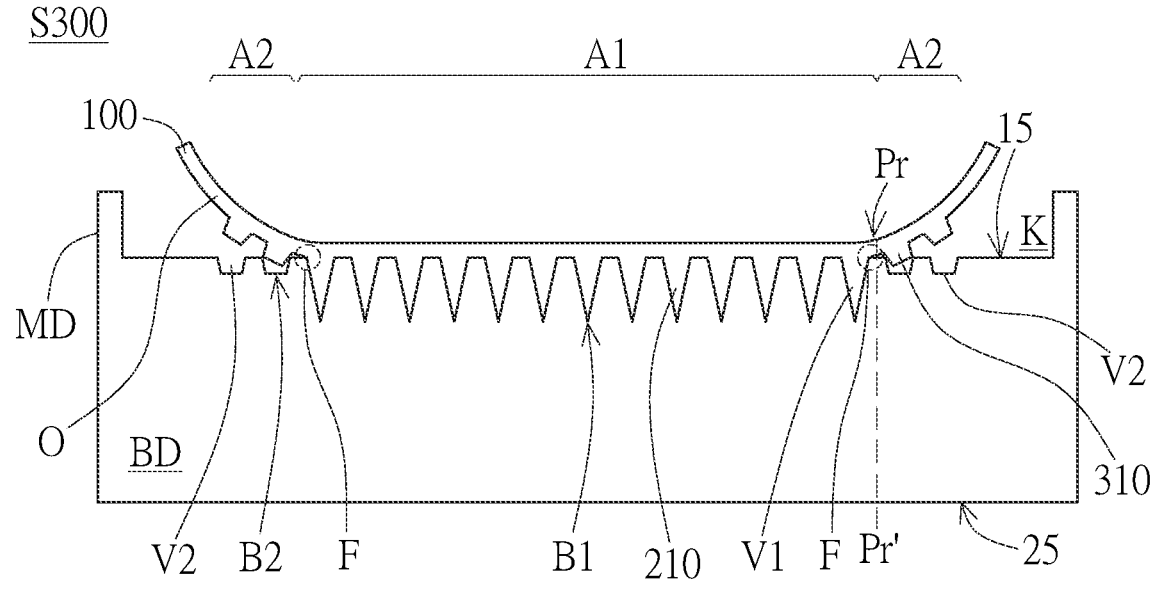
FIG. 15 is a schematic diagram of implementing a removal step of a manufacturing method according to an embodiment of the present invention.

Next, referring to FIG. 15, for example, but not limited to, after curing the coating material Q to form a body O of the transdermally deliverable microneedle patch under a predetermined condition as shown in the above FIG. 14A and FIG. 14B, the removal step S300 may be subsequently proceeded. In detail, according to this embodiment, the body O may be removed from the manufacturing mold MD from the second block A2 toward the first block A1. Therefore, a case in which the stress generated when the body O is removed from the manufacturing mold MD directly reaches or impacts the formed microneedles 210 along the basal layer 100 can be alleviated or eliminated.

Figure 16:
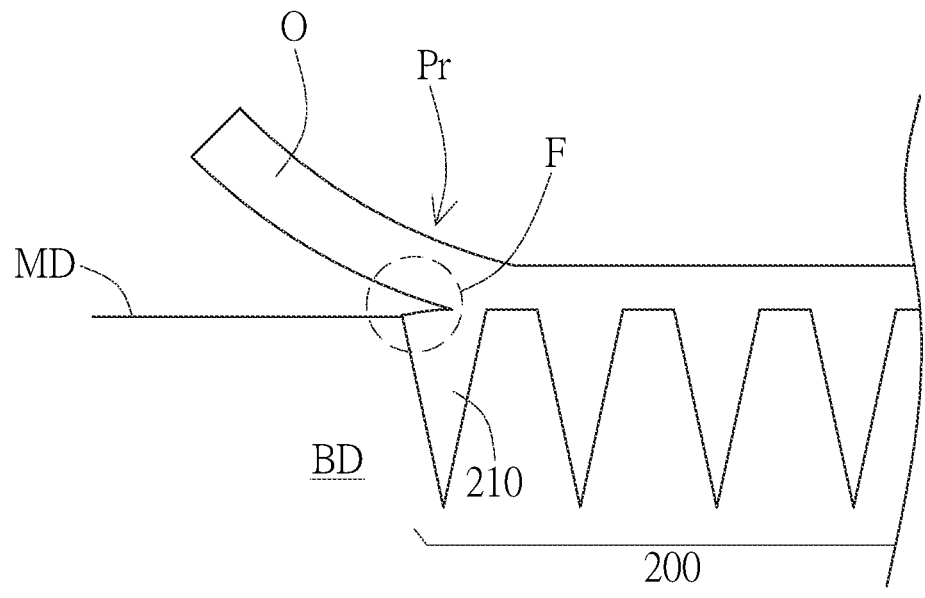
FIG. 16 is a schematic diagram showing an area prone to damage, bending, indentation, or fracture caused by concentrated stress according to an embodiment of the present invention.

Specifically, the stress generated in the removal step S300 may be first transmitted to the formed bump 310, and may be guided by the bump 310 to change a direction or an angle, or may be absorbed or buffered by the bump 310. Therefore, referring to the comparative example of FIG. 16 in which the bumps 310 are not provided together with FIG. 15, an area is prone to damage, bending, indentation, or fracture as a result of administration of unexpected stress to the periphery Pr of the microneedle array 200 (that is, the periphery Pr' of the distribution range of the first concave hole V1), such as but not limited to an area F, and the damage, bending, indentation, or fracture can be reduced or avoided due to the action of the bumps 310.

Figure 17:
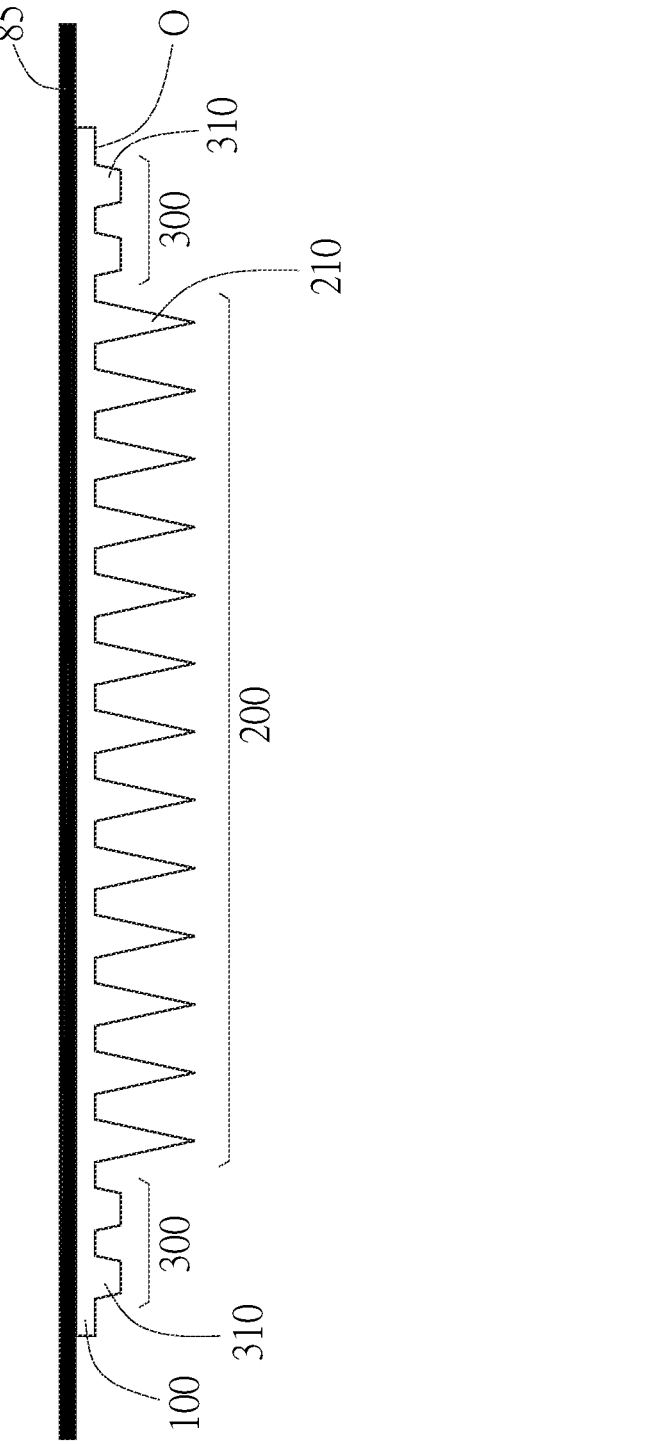
FIG. 17 is a schematic diagram of a transdermally deliverable microneedle patch completed by a manufacturing method according to an embodiment of the present invention.

Finally, referring to FIG. 17, after removing the body O of the transdermally deliverable microneedle patch, a transdermally deliverable microneedle patch 80 can be directly formed. Alternatively, the transdermally deliverable microneedle patch 80 may be manufactured through other additional processing procedure, for example, but not limited to sticking back adhesive 85 on a side of the basal layer 100 facing away from the microneedle array 200 and the bump array 300. However, the above additional processing procedure is merely an example, and other embodiments according to the present invention are not limited thereto. Carrying on with the above, any process or procedure that does not conflict with the technology of the present invention can be implemented in combination with the technology of the present invention, and these are not beyond the scope of the present invention.

Carrying on with the above, according to the manufacturing method 1000 and the manufacturing mold MD of the present invention, in the finally manufactured transdermally deliverable microneedle patch 80, the microneedles 210 may be formed corresponding to the first concave holes V1, and the bumps 310 may be formed corresponding to the second concave holes V2, so that the possible damage, bending, indentation, or fracture to the microneedles 210 can be reduced or avoided in the manufacturing process. Therefore, the number and structural integrity of the microneedles 210 of the transdermally deliverable microneedle patch 80 manufactured according to the manufacturing method 1000 and the manufacturing mold MD of the present invention can be improved, thereby ensuring or improving the accuracy of the dosage of the predetermined medicament M that is expected to be administered. Carrying on with the above, according to the present invention, the transdermally deliverable microneedle patch 80 can be more widely applied to various fields requiring dosage control, such as the field of medicine. In addition, a person of ordinary skill in the art should apply the manufacturing method 1000 and the manufacturing mold MD for manufacturing the transdermally deliverable microneedle patch 80 similarly or identically to manufacture the transdermally deliverable microneedle patches described in the above embodiments, for example, but not limited to the transdermally deliverable microneedle patches 10, 20, 30, 40, 50, 60, and 70.

Besides, the numbers of microneedles 210 and bumps 310 shown in the embodiments of the present invention are only examples, and the present invention is not limited thereto. In addition, proportions and relative proportions of the components or parts shown in the embodiments of the present invention that include the microneedles 210 and the bumps 310 may be enlarged or adjusted for clearer display, a person of ordinary skill in the art should understand that these are only examples, and actual dimensions should not be limited by those shown in the drawings.

Based on the above, according to the embodiments of the present invention, the damage, bending, indentation, or fracture of the drug-carrying microneedles on the transdermally deliverable microneedle patch can be reduced or avoided, and the dosage of the predetermined medicament can be further ensured. Therefore, the transdermally deliverable microneedle patch can be more widely applied in the fields such as aesthetic medicine, medicine, vaccines, and the like for subcutaneous injection. Therefore, according to the embodiments of the present invention, subcutaneous injection of more kinds of predetermined medicaments (for example, but not limited to painkillers, insulin, and vaccines) can be realized more conveniently and accurately under the condition of reducing or avoiding the pain that may be caused by the traditional subcutaneous injection means. Furthermore, it can also help to develop more transdermally deliverable microneedle patches that are convenient for people to carry and operate, and it can help to lower the threshold of technology or knowledge required for operation by setting a predetermined dosage, thereby simplifying and popularizing the procedure of administration more easily.

The above descriptions are only some preferred embodiments of the present invention. It should be noted that various changes and modifications can be made to the present invention without departing from the spirit and principles of the present invention. A person of ordinary skill in the art should clearly understand that the present invention is defined by the appended claims, and all possible changes such as substitutions, combinations, modifications, and diversions are within the scope of the present invention defined by the appended claims in line with the purpose of this invention.

REFERENCE NUMERALS

10, 20, 30, 40, 50, 60, 70, 80: transdermally deliverable microneedle patch
15: front side
25: back side
85: back adhesive
100: basal layer
200: microneedle array
210: microneedle
300: bump array
310: bump
1000: manufacturing method
A1: first block
A2: second block
B1, B2: bottom
BD: mold body
D1, D2: depth
E1, E2: end
F: area
G: through hole
H1, H2: height
K: accommodating cavity
L1, L2, L3, L4: diameter or maximum dimension
M: predetermined medicament
MD: manufacturing mold
O: body
Pr, Pr': periphery
Q: coating material
R: carrier component
R1: first dissolvable carrier component
R2: second dissolvable carrier component
R3: third dissolvable carrier component
S0: stratum corneum
S1: epidermis
S2: dermis
S100: coating step
S200: curing step
S300: removal step
V1: first concave hole
V2: second concave hole

What is claimed is:

1. A transdermally deliverable microneedle patch, comprising:
   a basal layer, for attaching to an epidermis;
   a microneedle array, arranged on the basal layer and comprising a plurality of microneedles that protrude and extend away from the basal layer, wherein the microneedles are made of a predetermined medicament and a first dissolvable carrier component, and diameters or maximum dimensions of the cross section of ends of the microneedles opposite to the basal layer are less than 50 μm; and
   a bump array, arranged on the basal layer and comprising a plurality of bumps that protrude and extend away from the basal layer, wherein diameters or maximum dimensions of the cross section of ends of the bumps opposite to the basal layer are greater than 50 μm; and
   the bumps are arranged at intervals along a periphery of the microneedle array, and heights by which the bumps protrude from the basal layer are less than heights by which the microneedles protrude from the basal layer, wherein the microneedles and the bumps are spaced apart from each other on the basal layer without overlapping, and wherein the plurality of microneedles are configured to pierce the epidermis and reach a dermis to release the predetermined medicament, and the plurality of bumps are configured to abut the epidermis such that the epidermis deforms or is pierced by the plurality of bumps when the plurality of microneedles pierce and reach the dermis.

2. The transdermally deliverable microneedle patch according to claim 1, wherein the heights by which the microneedles protrude from the basal layer are between 100 μm and 1500 μm.

3. The transdermally deliverable microneedle patch according to claim 1, wherein the heights by which the bumps protrude from the basal layer are between 10 μm and 150 μm.

4. The transdermally deliverable microneedle patch according to claim 1, wherein the bumps are made of the predetermined medicament and the first dissolvable carrier component.

5. The transdermally deliverable microneedle patch according to claim 1, wherein the bumps are made of a dissolvable carrier component, and the dissolvable carrier component is the first dissolvable carrier component or a second dissolvable carrier component different from the first dissolvable carrier component.

6. The transdermally deliverable microneedle patch according to claim 1, wherein the diameters or maximum dimensions of the cross section of the ends of the microneedles opposite to the basal layer are greater than 3 μm.

7. The transdermally deliverable microneedle patch according to claim 1, wherein the microneedles are polygonal pyramids or cones, and the bumps are polygonal columns, cylinders, incomplete spheres, or incomplete ellipsoids.

* * * * *